United States Patent [19]

Kennedy et al.

[11] 4,181,634

[45] * Jan. 1, 1980

[54] MILD CLEANSING COMPOSITIONS COMPRISING AN ALKYLENEOXYLATED BISQUATERNARY AMMONIUM COMPOUND AND AN ANIONIC OR AMPHOTERIC DETERGENT SUCH AS A PHOSPHOBETAINE

[75] Inventors: Robert R. Kennedy, Parlin; Martin K. O. Lindemann, Bridgewater; Robert J. Verdicchio, Succasunna, all of N.J.

[73] Assignee: Johnson & Johnson, New Brunswick, N.J.

[*] Notice: The portion of the term of this patent subsequent to Aug. 29, 1995, has been disclaimed.

[21] Appl. No.: 902,121

[22] Filed: May 5, 1978

Related U.S. Application Data

[63] Continuation-in-part of Ser. No. 807,768, Jun. 17, 1978, Pat. No. 4,110,263.

[51] Int. Cl.² .................. C11D 1/94; C11D 1/90; C11D 1/88; C11D 1/62
[52] U.S. Cl. .................. 252/545; 252/547; 252/DIG. 5; 252/DIG. 7; 252/DIG. 13
[58] Field of Search ............... 252/545, 547, DIG. 5, 252/DIG. 13, DIG. 7; 260/924, 945

[56] References Cited

U.S. PATENT DOCUMENTS

| | | | |
|---|---|---|---|
| 2,774,786 | 12/1956 | Erickson | 260/945 X |
| 3,507,937 | 4/1970 | Zimmerer | 252/545 X |
| 3,856,893 | 12/1974 | Diery et al. | 260/945 X |
| 3,876,563 | 4/1975 | Collins | 252/545 |
| 3,950,417 | 4/1976 | Verdicchio et al. | 252/545 |
| 4,110,263 | 8/1978 | Lindemann et al. | 252/545 |

*Primary Examiner*—Harris A. Pitlick
*Attorney, Agent, or Firm*—Steven P. Berman

[57] ABSTRACT

Mild cleansing compositions comprising at least one detergent and at least one alkyleneoxylated bisquaternaryammonium compound are described. Suitable bisquaternary ammonium compounds are represented by the formula

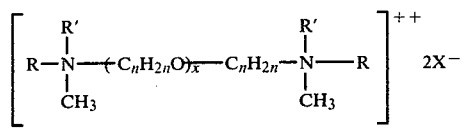

wherein R is an aliphatic radical of from about 10 to about 26 carbon atoms, R' is methyl, ethyl, propyl or R, X is an anion, n is an integer from 2 to 3, and x is an integer of from 1 to about 30. Suitable detergents are anionic or amphoteric detergents. The addition of alkyleneoxylated bisquaternary ammonium compound to anionic and amphoteric detergents reduces the irritant properties of the detergents.

10 Claims, No Drawings

MILD CLEANSING COMPOSITIONS COMPRISING AN ALKYLENEOXYLATED BISQUATERNARY AMMONIUM COMPOUND AND AN ANIONIC OR AMPHOTERIC DETERGENT SUCH AS A PHOSPHOBETAINE

This application is a continuation-in-part of pending Application Ser. No. 807,768, filed June 17, 1977, now U.S. Pat. No. 4,110,263.

The present invention relates to mild cleansing compositions, particularly fluid detergent compositions suitable for cosmetic purposes such as shampoo, bubble baths, baby baths, and the like.

BACKGROUND OF THE INVENTION

Cosmetic cleansing compositions not only must have cleansing action but must be non-irritating to the skin and the eyes. The major use for cosmetic cleansing compositions is in shampoos; other uses include liquid skin cleanser, baby baths, bubble baths and the like. A suitable detergent for shampoos must remove the surface grease and leave the hair and scalp clean. In addition it should leave the hair lustrous, soft and manageable; still further, it is desirable that it has good lathering properties for consumer acceptability.

Synthetic detergents include anionics, cationics, amphoterics and nonionics. The detergents generally having the most superior properties in terms of foaming, cleaning and end result attributes are the anionic detergents. Thus, most shampoo and cleansing formulations contain anionic detergents. These detergents however have a tendency to be very irritating to the skin and the eyes. For this reason anionic detergent compositions usually are modified by substituting a significant amount of nonionic detergents which are generally mild although of less effective cleansing ability. Certain amphoteric detergents are reported to have a low eye irritation potential. In an article on "Baby Shampoos" by H. S. Mannheimer, American Perfumer, 76, 36–37 (1961), there is described surface active agents which are complexes of an anionic surface active agent and a particular type of amphoteric surface active agent and which are urged to be non-irritating to the eyes. A number of similar compositions are available commercially and while they are milder than conventional shampoos, they are still found to be irritating. Thus, there is still a need for a shampoo and other cosmetic cleansing compositions in which irritancy can be substantially eliminated.

In several U.S. patents there are described compositions in which both amphoteric and nonionic surfactants are incorporated in anionic surfactant compositions. Thus, in U.S. Pat. Nos. 2,999,069 and 3,055,836 there are described shampoo compositions comprising certain mixtures of ethoxylated anionic, amphoteric and polyethoxylated nonionic surfactants. Further, in U.S. Pat. No. 3,928,251 there are described shampoo compositions comprising certain mixtures of anionic, nonionic and zwitterionic surfactants. Similarly, in U.S. Pat. No. 3,950,417 shampoo compositions are described for which low ocular irritancy is urged; in these compositions nonionic and amphoteric surfactants have been added to modify anionic surfactants. All of these compositions include a nonionic detergent as an essential component.

Cationic detergents are usually poor in detergency and also harsh to skin and eyes. Thus, beside the certain amphoteric imidazolium compounds, detergents having a positively charged hydrophilic portion are not usual components of cosmetic cleansing compositions.

Although compounds having two terminal polar groups which embrace acid, ester, amide, hydroxyl, amine, quaternary ammonium, sulfate, sulfonate, etc. and which contain a cyclic moiety in the divalent chain between the polar groups are broadly urged to be useful as mildness additives for various detergents (U.S. Pat. Nos. 3,538,009; 3,630,934; 3,769,242; 3,798,182; 3,813,350; 3,947,382), acyclic alkyleneoxylated bisquaternary ammonium compounds are not known to have mildness imparting properties and have not been formulated in shampoo or cosmetic cleansing compositions. Alkyleneoxylated bisquaternary ammonium compounds have been employed as antistatic agents for fibers, U.S. Pat. No. 3,954,633 (corr. German 2,335,675); wetting and washing agents and as dressing for artificial silk, British Pat. No. 474,671; agents for treating clays to prevent swelling, U.S. Pat. No. 3,349,032; agents for imparting water resistant properties to felts, German Pat. No. 2,509,741; and when employed as a perchlorate, as photographic sensitizers, U.S. Pat. No. 2,944,902. Although certain alkyleneoxylated monoquaternary ammonium compounds are taught in hair rinsing compositions for improving combing properties (U.S. Pat. No. 3,155,591) their use in shampoo or cosmetic cleansing compositions are not known. Quaternary ammonium compounds are not expected to be useful in compositions which have low eye irritation potential. In an article entitled "Shampoos" by D. H. Powers, in "Cosmetics: Science and Technology," Wiley-Interscience, 1972, the author points out on pages 94 and 96, the harshness and irritation to eyes and skin of cationic detergents or compounds with cationic tendency. Thus, it is unexpected that by the compositions and methods of the present invention it has been possible to greatly reduce eye irritation potential below that of the mildest compositions heretofore known without reducing the effective cleansing properties.

BRIEF STATEMENT OF INVENTION

According to the present invention cosmetic cleansing compositions are obtained in which mildness is achieved without the necessity of employing nonionic detergents and which substantially eliminates the ocular irritancy still existing in the heretofore available shampoos. The cosmetic cleansing compositions of the present invention comprise a detergent component in admixture with an alkyleneoxylated bisquaternary ammonium compound component. The detergent component comprises at least one detergent which may be an anionic detergent or an amphoteric detergent or it may be a mixture of anionics, of amphoterics or both. The addition of a minor proportion of an alkyleneoxylated bisquaternary ammonium compound as hereinafter defined so decreases the ocular irritancy and ocular harm produced by the most useful anionic and amphoteric cleansing detergents that cosmetic cleansing compositions may be formulated maximizing the cleansing properties of the detergent and still be rendered mild and desirable for use. This is quite unexpected when it is realized that cationic compounds are known ocular and skin irritants. It has further been discovered that not only does the incorporation of the bisquaternary ammonium compounds impart mildness properties to cleansing compositions known to have irritating properties but significantly decreases and substantially eliminates the ocular irritation of the heretofore known so-called mild shampoo compositions which had been formulated by the incorporation of nonionic detergents or of certain imidazolium amphoteric detergents. Thus, the invention embraces a method for imparting mildness properties to a cosmetic cleansing composition by adding thereto a minor proportion of an alkyleneoxylated bisquaternary ammonium compound as hereinafter defined.

DETAILED DESCRIPTION OF THE INVENTION

In the novel cosmetic cleansing compositions of the present invention comprising a detergent component and an alkyleneoxylated bisquaternary ammonium compound component, the alkyleneoxylated bisquaternary ammonium compounds may be represented by the formula

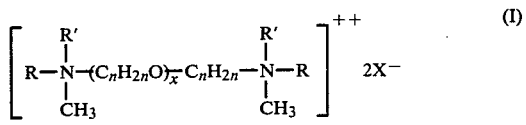

wherein each R is an aliphatic radical of from about 10 to about 26 carbon atoms, R' is methyl, ethyl, propyl or R, X is an anion, n is 2 or 3, and x is an integer of from 1 to about 30.

Thus, in the alkyleneoxylated bisquaternary ammonium compounds (which hereinafter may be referred to merely as "the quaternary ammonium compounds" or "bisquaternary ammonium compounds"), the expression "alkyleneoxylated" refers to the alkyleneoxy bridge, which is joined to the nitrogen through a carbon. In the compounds, the alkyleneoxy bridge is of at least five atoms, i.e., in the formula x is 1. In the preferred bisquaternary ammonium compounds, the nitrogens are separated by sixteen or more carbon atoms, i.e., in the formula, x is 7 or greater. The alkylene chain between the oxygens contain from 2 to 3 carbon atoms. Preferably, the alkylene group is ethylene. Each quaternary nitrogen is substituted with at least one long chain alkyl radical of at least 10 carbon atoms; it may be substituted with two long chain alkyl radicals. Suitable radicals include decyl, dodecyl, octadecyl, tetradecyl, hexadecyl, octadecyl, eicosyl, docosyl, tricosyl, hexacosyl, and the like. The nature of the anion is not critical, however, it should be compatible with the detergent and should be of the type stable in aqueous media. It is usually a water-soluble anion of common inorganic or organic acids, such as ascorbate, bromide, chloride, gluconate, methylsulfate, benzoate, lactate, citrate, salicylate, acetate, formate, N,N-diethyl-p-aminobenzoate, and the like. Although it may be an anionic detergent group, it is contemplated that the quaternary compound be supplied in a form containing the more simple anions and the detergent type anionic group be supplied in a more conventional form as a commercially available anionic detergent.

In order to more readily identify the length of the chain between the quaternary nitrogens as well as to simplify the name of the compounds when x in the foregoing formula is greater than 1, a nomenclature is employed herein which indicates the number of alkylene oxide units in the compound by the prefix which corresponds to x when x is greater than 1. The nomenclature is illustrated with some of the compounds as follows (In the first compound, the preferred chemical nomenclature is also employed):

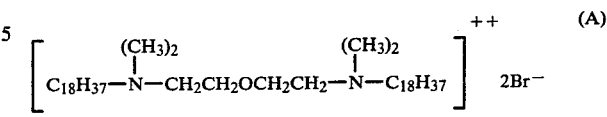

ethyleneoxyethylene-bis-(dimethyl-octadecylammonium bromide)
[Preferred chemical nomenclature: N,N-dioctadecyl-N,N,N'N'-tetramethyl-1,5(3-oxapentylene)diammonium bromide]

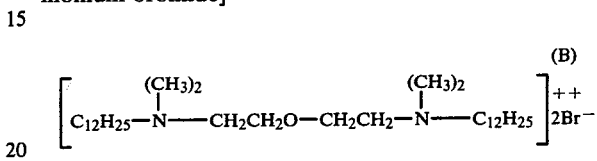

ethyleneoxyethylene-bis(dodecyl-dimethylammonium bromide)

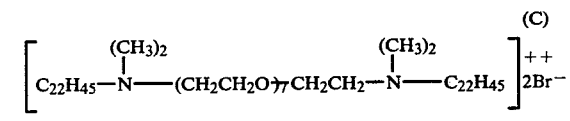

hepta(ethyleneoxy)ethylene-bis(docosyl-dimethylammonium bromide)

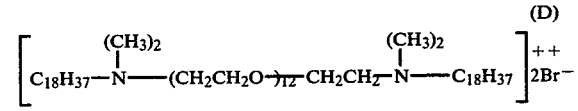

dodeca-(ethyleneoxy)ethylene-bis(dimethyl-octadecylammonium bromide)

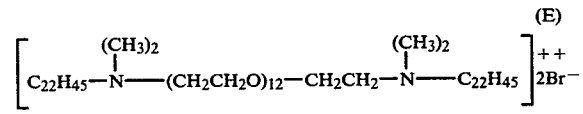

dodeca-(ethyleneoxy)ethylene-bis-(docosyl-dimethylammonium bromide)

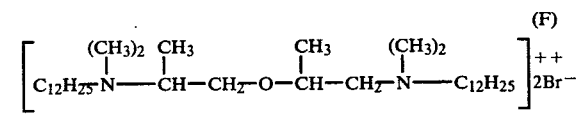

propyleneoxypropylene-bis(dodecyl-dimethylammonium bromide)

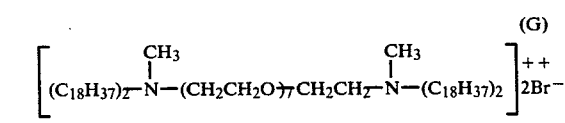

hepta(ethyleneoxy)ethylene-bis(methyl-dioctadecylammonium bromide

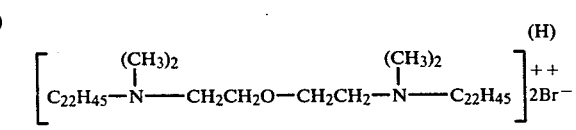

ethyleneoxyethylene-bis(docosyl-dimethylammonium bromide)

-continued

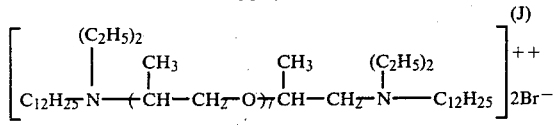

hepta(propyleneoxy)propylene-bis(dodecyl-diethylammonium bromide)

The preferred bisquaternary ammonium compounds may be represented by the formula

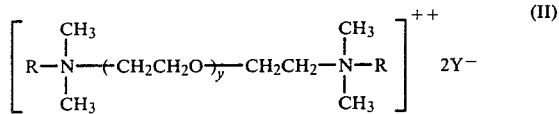

wherein R is an aliphatic radical of from about 10 to about 26 carbon atoms, Y is halide and y is an integer of from about 7 to about 14.

Many of the bisquaternary ammonium compounds employed in the novel compositions of the invention are novel compounds. The compounds may be prepared from an appropriate polyalkylene glycol and an appropriate amine by first halogenating, preferably brominating, the appropriate polyalkylene glycol to produce a polyoxyalkylene halide and thereafter reacting the resulting polyoxyalkylene halide with an appropriate amine to produce the bisquaternary ammonium compound. The halide may be replaced by other anions, if desired, by employing conventional procedures.

In a representative operation, phosphorous tribromide is added dropwise with stirring to the appropriate polyalkylene glycol while the reaction mixture is maintained at a temperature in the range of from about 0° to about 5° C. After completion of the addition the reaction mixture is stirred for several hours, preferably for about 24 hours, to complete the reaction with the formation of the polyoxyalkylene dibromide. The mixture is allowed to warm up to room temperature and the dibromide is recovered by carefully adding water to the reaction mixture to precipitate the dibromide which then is isolated in a conventional manner. To the dibromide thus prepared then is added a methanolic solution of a tertiary amine, preferably a dialkyl-(long-chain-alkyl)amine, to produce the desired bisquaternary ammonium bromide which generally remains in the reaction mixture. The product bisquaternary ammonium bromide may be separated from the reaction mixture by adding excess acetone to the mixture to precipitate the bromide and thereafter filtering off the precipitate.

The detergent component contains at least one anionic or amphoteric detergent and may contain both types of detergents.

Suitable anionic detergents may be selected from various classes including salts of fatty alcohol and fatty acylamino polyethyleneoxylated (polyethoxylated) sulfates, sulfonates, and succinates; primary alkyl sulfates; alkylbenzene sulfonates; alkyl monoglyceride sulfates; acyl sarcosinates; sulfosuccinates; acylesters of isethionic acid; acyl-N-methyl taurides and condensation products of fatty acid chloride with protalbinic or lysalbinic acids. The alkyl or acyl radical in the foregoing usually contains from about 8 to about 20 carbon atoms. Preferred are alkyl or acyl containing from about 12 to 18 carbon atoms. Since the detergents are normally prepared using naturally occurring fatty alcohols and acids, the long chain groups are generally mixed alkyl and/or mixed saturated and unsaturated although a particular alkyl or acyl group predominates. Thus, when reference is made herein to an alkyl of a particular chain length in connection with a detergent, it may designate the presence not only of the named alkyl but also of minor amounts of other groups, particularly groups normally associated with it in the naturally occurring source. The detergents are employed in the form of salts in which the cationic portion is a non-toxic metal, ammonium or substituted ammonium group such as sodium, potassium, triethanolammonium, diethanolammonium, diisopropanolammonium, and the like.

The preferred anionic detergents are the polyethyleneoxylated anionic detergents, particularly the salts of fatty alcohol and fatty acylamino sulfates and sulfonates in which there is an ethyleneoxy chain between the functional group and the fatty acid or alcohol derived hydrocarbon portion. (It is here noted that "polyethyleneoxylated" is sometimes referred to in the art as "polyethoxylated.") The polyethyleneoxylated anionic detergents may be represented by the formula $$R_1-(O-CH_2CH_2)_{2-4}-Y^- M^+ \quad (III)$$

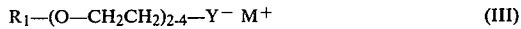

In this and subsequent formulas, $R_1$ is alkyl containing from about 8 to 20 carbon atoms, alkylphenyl wherein the alkyl portion contains from about 6 to about 15 carbon atoms, and acylamino wherein the acyl contains from about 8 to about 16 carbon atoms; Y is sulfate or sulfonate; M is a non-toxic water soluble cation, preferably alkali metal ammonium or a substituted, preferably hydroxyalkyl substituted ammonium. Preferred of the foregoing are alcohol ether sulfates in which $R_1$ in the foregoing formula is alkyl and Y is sulfate and which may be represented by the formula $$C_8-C_{20} \text{ alkyl-}(O-CH_2CH_2)_{2-4}-OSO_3^-Na^+$$

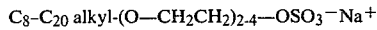

Preferably, the alkyl contains from about 10 to 14 carbon atoms, e.g., lauryl, tridecyl, decyl, undecyl, and the like, and there are three or four ethyleneoxy groups. It is noted here that in the detergent art, the nomenclature employed frequently identifies the number of the polyethyleneoxy groups by parenthetical numerical designation following the word "ether" or "polyoxyethylene" or "polyethyleneoxy" or "polyethoxylate." Thus, a detergent which may be characterized by having "tridecyl" as the higher alkyl group, four ethyleneoxy groups and sodium as the cationic group may be called "tridecyl alcohol ether (4) sodium sulfate" or "sodium polyethoxylated (4) tridecyl alcohol ether sulfate" or "sodium tridecyl polyoxyethylene (4) ethyl sulfate" or variations thereof. Representative alcohol ether sulfates include sodium polyethyleneoxylated (4) tridecylalcohol sulfate, sodium polyethyleneoxylated (4) tridecyl alcohol ether sulfate, sodium polyethyleneoxylated (4) coconut fatty alcohol ether sulfate, ammonium polyethyleneoxylated (3) tetradecyl alcohol ether sulfate, triethanolammonium polyethyleneoxylated (2) 2-ethyltetradecanol sulfate; potassium polyethyleneoxylated (3) tridecanol ether sulfate, diethanolammonium polyethoxylated (4) dodecane-2-ol-ether sulfate, and the like.

Polyethyleneoxylated alkylphenol ether sulfates and sulfonates are also suitable as anionic detergents. They are similar in structure to the alcohol ether sulfate and sulfonates, but having an alkylphenyl group instead of an alkyl group. Representative of the foregoing include sodium polyethyleneoxylated (4) nonylphenol ether sulfate, potassium polyethyleneoxylated (4) octylphenol ether sulfate, sodium polyethyleneoxylated (4) pentadecylphenol ether sulfate, sodium polyethyleneoxylated (2) p-tertiary octylphenol ether sulfate, sodium lauryl ether (2) sulfate, etc. Representative polyethyleneoxylated acylamino (or acid amido) ether sulfates and sulfonates include sodium salt of sulfated polyethyleneoxylated (4) lauroylamide, potassium polyethyleneoxylated (4) caprylamide ether sulfate, triethanolammonium polyethyleneoxylated (5) hexadecoyl ether sulfate, etc.

Other polyethyleneoxylated anionic detergents are polyethyleneoxylated mono fatty alcohol sulfosuccinates. These are generally derived from $C_{10}$-$C_{14}$ mono fatty alcohols forming a monoester through an ethyleneoxy chain of about two to four ethyleneoxy groups; preferably they are in the form of sodium salts. Representative examples of such sulfosuccinates are sodium polyethyleneoxylated (3) lauryl alcohol sulfosuccinate monoester, potassium polyethyleneoxylated (2) octanol sulfosuccinate monoester, triethanolammonium polyethyleneoxylated (2) hexadecanol sulfosuccinate monoester, and the like.

Non-alkyleneoxy containing anionic detergents are also useful in the compositions of the present invention. Representative of these are alkyl sulfates such as sodium lauryl sulfate, triethanolammonium lauryl sulfate, and the like; alkyl monoglyceride sulfate represented by the structure

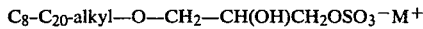
$$C_8\text{-}C_{20}\text{-alkyl}-O-CH_2-CH(OH)CH_2OSO_3^-M^+$$

wherein the alkyl is most preferably dodecyl, tetradecyl and hexadecyl; sarcosines represented by the structure

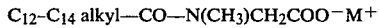
$$C_{12}\text{-}C_{14}\text{ alkyl}-CO-N(CH_3)CH_2COO^-M^+$$

especially lauroyl and coconut oil fatty acid derivatives of N-methylglycine such as sodium lauryl sarcosinate; sulfosuccinates or sulfosuccinamates, half esters or amides, respectively, of sulfosuccinic acid with longer chain alkyl, generally from about 8 to 20 carbon atoms such as dioctyl esters of sodium sulfosuccinic acid, decyl esters of sodium sulfosuccinic acid, sodium salt of coconut monoethanolamide sulfosuccinate, etc.; also N-(1,2-dicarboxyethyl)-N($C_{18}$ "alkyl")-sulfosuccinamate, etc. In addition, acylester of isethionic acid represented by

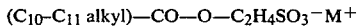
$$(C_{10}\text{-}C_{11}\text{ alkyl})-CO-O-C_2H_4SO_3^-M^+$$

and exemplified by coconut oil acid ester of sodium isethionate; N-acyl taurates represented by the structure

$$(C_{10}\text{-}C_{18}\text{ alkyl}) CONH-C_2H_4-SO_3^-$$

and exemplified by sodium methyl tallow acid taurate and potassium methyl lauroyl taurate; and condensation products of fatty acids with protalbinic and lysalbinic acids such as coconut condensate, in the form of sodium salts. The foregoing represents some of the typical anionic detergents suitable in the cleansing compositions of the present invention. Many other anionic detergents not classifiable in the foregoing structures are known and may be used in the cosmetic cleansing compositions of the present invention. Suitable anionic detergents are readily available under various trade names.

Suitable amphoteric detergents include those compounds which are zwitterionic, i.e., internally ionized and those which show acidic or basic properties only in appropriate media. Representative amphoteric detergent include betaines, sulfobetaines (sultaines) and phosphobetaines, N-alkyl-beta-iminodipropionates and N-alkyl-beta-aminopropionates; and compounds derived from 2-higher alkyl imidazoline, e.g., hydroxyethylcarboxymethyl alkyl imidazolium salts.

One group of amphoteric detergents are the betaine compounds. The expression "betaine compounds" as herein employed is intended to embrace betaines and sultaines, and alkyl and acylaminoalkyl derivatives of either. The acylaminoalkyl derivatives are generally known in the art as amidobetaines. A preferred group of betaine compounds may be represented by the formula

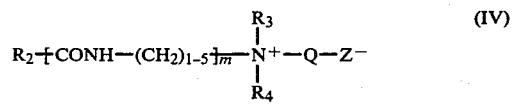
$$R_2\text{-}\!\!\left[CONH-(CH_2)_{1-5}\right]_{\overline{m}}\!\!\!\!\!\overset{R_3}{\underset{R_4}{-N^+-Q-Z^-}} \quad (IV)$$

In this and succeeding formulas, $R_2$ is a higher alkyl group containing from 8 to 20 carbon atoms; $R_3$ and $R_4$ are lower alkyl groups containing from 1 to about 4 carbon atoms; Q is an alkylene group of from 1 to 3 carbon atoms or a hydroxyalkylene group of from 2 to 3 carbon atoms; Z is carboxylate, $-COO^-$, or sulfonate, $-SO_3^-$; provided that when Z is $-COO^-$, Q is alkylene; and m is 0 or 1. Suitable $R_2$ group include decyl, dodecyl, hexadecyl, octadecyl, eicosyl and the like. $R_3$ and $R_4$ may be represented by methyl, ethyl, propyl, isobutyl, etc. Within the foregoing formula representative alkyl betaines include decyl betaine (i.e., N-decyl dimethylglycine), dodecyl betaine, tetradecyl betaine, cetyl betaine, stearyl betaine, coco betaine, and the like; representative amido betaines include cocoamido propyl betaine (N-(3-coconut acylaminopropyl)N,N-dimethyl 2-amino acetate) laurylamidomethyl betaine, myristylamidomethyl betaine, palmitylamidomethylbetaine, stearylamidomethyl betaine, and the like. Representative alkyl sulfobetaines include coco-dimethylsulfopropylbetaine, stearyldimethylsulfopropylbetaine, and the like; representative amido sulfobetaines include cocoaminomethyldimethylsulfopropylbetaine (N-cocoyl (dimethylamino)propane sulfonate), stearylaminomethyldimethylsulfopropylbetaine, myristylaminomethyldimethylsulfopropyl betaine, laurylaminomethyl-bis-(2-hydroxyethyl)-sulfopropylbetaine, (3-(N,N-dimethyl-N-laurylamino)2-hydroxypropanesulfonate), and the like.

A closely related group of compounds to the defined betaine compounds, i.e., betaines and sulfobetaines, are the phosphobetaine compounds. These compounds may be represented by the following formulas:

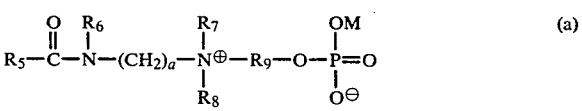

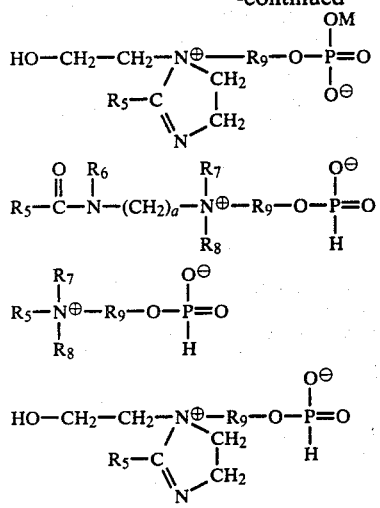

wherein $R_5$ is straight or branched chain alkyl, alkenyl, arylalkyl or cycloalkyl containing from 6 to 26 carbon atoms; $R_6$ is hydrogen, straight or branched chain alkyl, alkenyl, cycloalkyl or hydroxyalkyl containing from 1 to 6 carbon atoms; $R_7$ and $R_8$ may be the same or different and are straight or branched chain alkyl or hydroxyalkyl containing from 1 to 6 carbon atoms or a polyoxyalkylene ether radical of the formula $$(R'-O)-R''$$

wherein $R'$ and $R''$ are alkylene and alkyl, respectively, containing from 1 to 4 carbon atoms and b is an integer from 2 to 10; $R_9$ is straight or branched chain alkylene or hydroxyalkylene containing from 1 to 6 carbon atoms; M is straight or branched chain alkyl or hydroxyalkyl containing from 1 to 6 carbon atoms, polyhydroxyalkyl containing from 1 to 6 carbon atoms, alkali metal, alkaline earth metal or a substituted ammonium compound such as mono-, di- or triethanolamine; and a is an integer from 1 to 5.

Representative phosphobetaine compounds include compounds having the following structures:

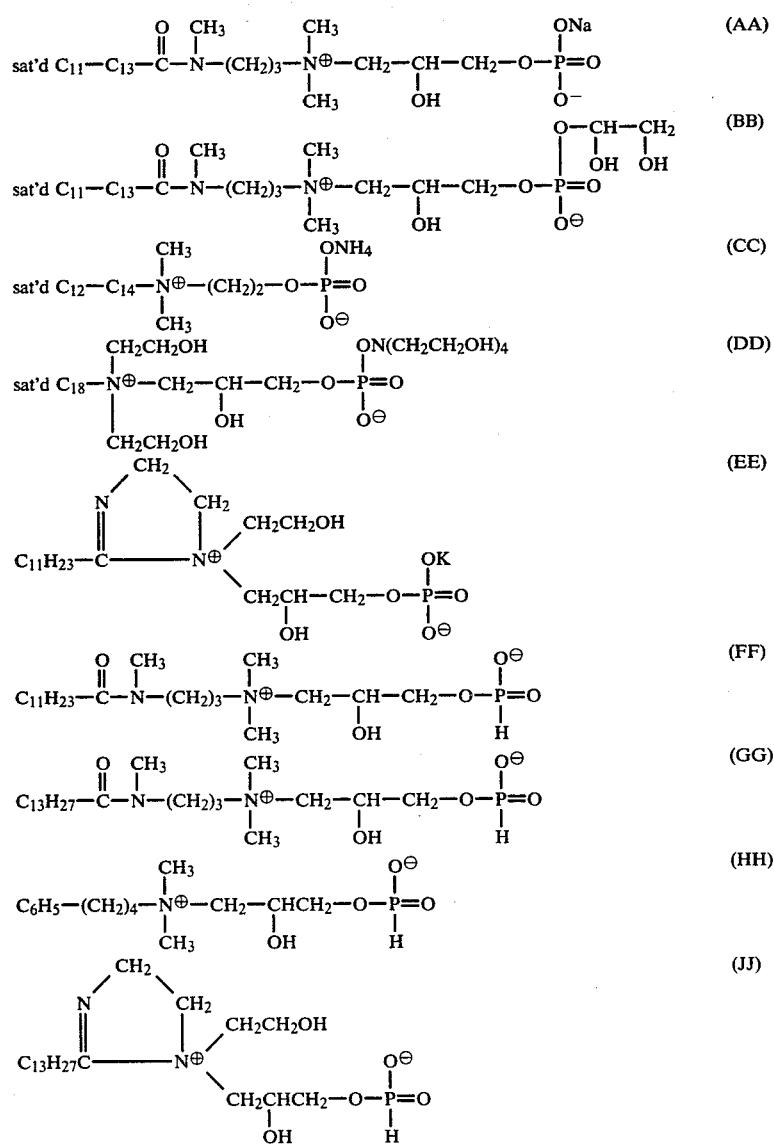

These phosphobetaine compounds can be prepared by reacting a fatty acid containing from 6 to 26 carbon atoms or mixtures thereof such as lauric, myristic, tallow and the like with a diamine containing at least one tertiary amino group such as dimethylamino-propylamine to form an amidoamine intermediate.

Epichlorohydrin is separately reacted with monosodium or disodium hydrogen phosphate to form an epibiphosphate intermediate. The epibiphosphate intermediate is used to alkylate the amidoamine intermediate to form the desired amidophosphobetaine. Fatty tertiary amines can be alkylated in the same manner to form the corresponding aminophosphobetaines.

The corresponding amido-aminophosphite compounds can be prepared in a similar manner utilizing an epibiphosphite intermediate prepared from the reaction of a monosodium or disodium orthophosphite with epichlorohydrin. This intermediate is used to alkylate the amidoamine intermediate on the fatty tertiary amine to form the corresponding amido or aminophosphite compounds.

Another important group of amphoteric detergents are the N-alkyl-iminodipropionates and N-alkyl-aminopropionates. The preferred of these compounds may be represented by the formula

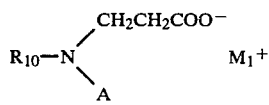

wherein $R_{10}$ is alkyl from 8 to 20 carbon atoms; A is hydrogen or $—CH_2CH_2COO^-$ and $M_1$ is hydrogen or a non-toxic salt forming cationic group such as an alkali metal (e.g. sodium, potassium), ammonium or substituted ammonium (e.g., diethanolammonium, ethanolammonium, triethanolammonium) cation. Representative N-alkyl-β-aminopropionates include sodium salt of N-lauryl-β-aminopropionate, sodium salt of N-coco-β-aminopropionic of N-coco-β-aminopropionic acid, and the like. Representative N-alkyl-β-iminodipropionates include disodium N-lauryl-β-iminodipropionate, N-lauryl myristyl-β-iminodipropionate, and N-tallow-β-iminodipropionate and the like.

Another class of suitable amphoteric detergents are the zwitterionic imidazolium salts. These detergents may be represented by

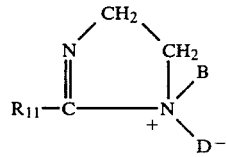

In this and succeeding formulas, $R_{11}$ is a higher alkyl or alkenyl radical of from 8 to 20 carbon atoms; and D is $—CH_2COO^-$ or $—CH_2SO_3^-$. Although these amphoteric detergents are generally named as imidazolium salts, a significant portion appears to exist in the open chain or uncyclized form is solution. The uncyclized form may be represented by

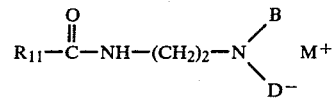

(The relationship may be seen more fully, for example, with the sulfonates in British 989,497.)

The preferred detergents of this class may be represented by the formula

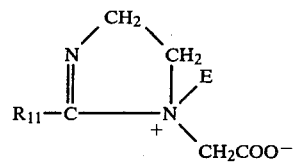

wherein E is $—CH_2CH_2OH$ or $—CH_2CH_2OCH_2COO^-$, or by the corresponding open chain formula. Representative imidazolium salts include those in which the $R_{11}$ derived from is coconut, lauric, caprylic, myristic, capric, linoleic, oleic acids and the like.

While other anionic and amphoteric detergents are within the scope of the compositions of the present invention, the foregoing are considered to be preferred for cosmetic cleansing formulations. However, since all liquid detergents are a potential irritation hazard, the bisquaternary ammonium compounds as hereinbefore defined may be added to anionic and amphoteric detergents which are not primarily cosmetic cleansing compositions to render them more desirable. Hence, the present invention embraces a method of reducing ocular irritancy of anionic and amphoteric detergents whether cosmetic compositions or not by incorporating therein a minor proportion of an alkyleneoxy bisquaternary ammonium compound.

In a preferred embodiment of the present invention, the detergent component is a mixture of an anionic and an amphoteric detergent. A particularly preferred embodiment is one in which the detergent component is a 2:1 to 1:2 mixture of a polyoxyethylated anionic detergent represented by Formula III, and a betaine compound or phosphobetaine compound amphoteric detergent represented by Formula IV or Formulas a-f. These are formulated with a preferred bisquaternary ammonium compound represented by Formula II.

The essential components in the cleansing compositions of the present invention are the detergent component and the alkyleneoxylated bisquaternary ammonium compound component. The detergent component contains at least one anionic or amphoteric detergent and the alkyleneoxylated bisquaternary ammonium compound component contains at least one alkyleneoxylated bisquaternary ammonium compound. The detergent component may be of a single detergent or a mixture of detergents of the same or different class. The relative amount of bisquaternary ammonium compound to detergent is from about 0.01 to about 0.3 part for each part of detergent. A more preferred range is from about 0.17 to 0.2 part of bisquaternary ammonium compound for each part of the detergent. The ratio is based on the total weight of the bisquaternary ammonium compound to the total weight of the active detergent. Thus, if a mixture of detergents is employed the ratio is based on the combined weights. When a mixture of detergents constitutes the detergent component, the relative amounts of each detergent are generally determined by consideration of properties other than relationship to the quaternary ammonium compound. Usually when the detergent mixture is of an amphoteric and an anionic detergent, the ratio in a range of from 2:1 to 1:2 by weight is employed, most preferably 1:1. In addition to the foregoing, water is used to complete the composition. The detergent component is generally present in an amount from about 4 percent to about 40 percent of the total weight of composition, the bisquaternary ammonium compound in an amount from about 0.01 to 0.3 part for each part by weight of detergent, and the remainder is primarily water. The concentration of the detergent in a liquid composition suitable for ultimate use is preferably in the range of about 10 to 20 percent by weight. Concentrate compositions and semisolid compositions such as gels and creams generally have higher amounts.

In addition, other ingredients conventionally added to shampoo or cosmetic bath compositions, such as dyes, preservatives, perfumes, thickeners, opacifiers, conditioners, buffering agents, etc., may be added in minor amounts. Dyes, preservatives and perfumes together usually constitute less than 1 percent of the total composition. Thickeners may be added to an amount of from about 1 to about 3 percent. Nonionic detergents do not constitute an essential component of the present invention. By employing the bisquaternary ammonium compounds with the anionic and/or amphoteric detergents, the less effective nonionic detergent may be omitted. However, it has been found that the bisquaternary ammonium compounds improves the properties of even those compositions containing nonionic detergents and which heretofore had been considered an improved shampoo composition. Thus, nonionic detergents may be considered a non-essential optional material which may be included; the nonionic detergents which are useful include the alkylene oxide ethers of phenols, fatty alcohols, and alkyl mercaptans; the alkylene oxide esters of fatty acids; the alkylene oxide ethers of fatty acid amides; the condensation products of ethylene oxide with partial fatty acid esters, and mixtures thereof. The polyoxyalkylene chain in such agents may contain from 5 to 30 alkylene oxide units in which each alkylene unit has from 2 to 3 carbon atoms. In addition, buffering agents may be added but usually the compositions are self buffering so that additional buffering agents are not necessary. Only ingredients which are not irritating to the eye are added.

The detergent compositions of the present invention may be concentrate compositions which are subsequently modified by dilution with water or other diluents to provide the ultimate compositions for use or they may be the ultimate cleansing compositions to be employed without modification. The compositions are primarily useful in shampoo formulations having high foaming characteristics and low ocular irritation as well as low ocular harm but may also be used in liquid soaps and cleansers such as baby bath compositions, in bubble bath compositions, as well as in compositions suitable for cleansing animals and inanimate objects.

The compositions may be prepared by mixing the surfactant and bisquaternary ammonium compound at ambient temperature, followed by warming to slightly elevated temperatures (about 50° C.) and thereafter adding deionized water to bring the composition to about three-quarters of the final intended weight. The pH is then adjusted to within the range of 4 to 8, preferably 6 to 8, and most preferably 7±0.3, by adding strong acid (e.g., HCl) or strong base (e.g., NaOH), as needed, and finally adding the remainder of the water. The pH is again adjusted and (if desired) other ingredients such as preservatives, dyes, perfumes, opaquing agents and the like are added.

The cosmetic cleansing composition of the present invention possess lower ocular irritation as shown by tests carried out to determine their effect on eye irritation. The test employed is the modified Draize Test (J. H. Draize et al, Toilet Goods Assn. No. 17, May, 1952, No. 1 Proc. Sci. Sect.).

In this method, a 0.1 ml. sample of a neutral composition under test is dropped into one eye of an albino rabbit, the other eye serving as a control. Six rabbits are employed for each composition.

Observations are made after 1, 24, 48, 72 and 96 hours and seven days after initial instillation; second and third instillations are made after the 24 and 48 hour readings. Results may vary from substantially no change or only a slight irritation in the appearance of the rabbit's eye after seven days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, etc.

The following examples illustrate the invention but are not to be construed as limiting:

EXAMPLE 1

Cleansing compositions with and without alkylene oxylated bisquaternary ammonium compounds having the components indicated below were prepared:

| INGREDIENT | COMPOSITION | | | |
|---|---|---|---|---|
| | A | B | C | D |
| | Percent by Weight | | | |
| Compound TL (34%)[1] | 35.32 | 35.32 | — | — |
| 15% HCl | 2.00 | 2.00 | — | — |
| Water | 62.68 | 58.68 | 43.41 | 47.41 |
| Compound C[2] | — | 4.00 | 4.00 | — |
| Oleoamido-sulfosuccinate di Na Salt (35%)[3] | — | — | 32.87 | 32.87 |
| Triethanolamine salt of tridecyl alcohol ether (4.2) sulfate (30%) | — | — | 19.72 | 19.72 |

[1] A commercial amphoteric/anionic complex consisting of a 1/1 molar ratio of 2-"lauroyl" - 1(sodium carboxymethyl)-1-(2-hydroxyethyl)-2-imidazolium hydroxide and tridecyl polyoxyethylene(4)sodium sulfate, 34% active detergent, product of Miranol Chemical Co., Irvington, N.J.
[2] In this and subsequent examples, where a bisquaternary ammonium compound is employed whose structure previously has been illustrated, the compound is identified by reference to the structure.
[3] In this and subsequent examples, percent active detergent is indicated parenthetically.

The compositions were employed to determine eye irritation by a modified Draize method and scored as previously described. The results were as follows:

TABLE I

| COMPOSITION | IRRITATION SCORE | | | | | |
|---|---|---|---|---|---|---|
| | 1 Hr. | 24 Hr. | 48 Hr. | 72 Hr. | 96 Hr. | Day 7 |
| A (Control) | 12.8 | 18.2 | 27.0 | 42.8 | 47.2 | 36.2 |

TABLE I-continued

| COMPOSITION | IRRITATION SCORE | | | | | |
|---|---|---|---|---|---|---|
| | 1 Hr. | 24 Hr. | 48 Hr. | 72 Hr. | 96 Hr. | Day 7 |
| B | 2.0 | 0.0 | 0.0 | 0.0 | 0.0 | 0.0 |
| C | 1.0 | 0.0 | 0.0 | 0.0 | 0.0 | 0.0 |
| D (Control) | 10.2 | 3.5 | 8.0 | 16.8 | 19.7 | 12.3 |

EXAMPLE 2

Shampoo compositions containing at least one bisquaternary ammonium compound and control compositions containing no bisquaternary ammonium compound and having the formulations indicated below were prepared in a conventional manner by intimately mixing the components:

TABLE II

| COMPOSITION | QUATERNARY COMPOUND Percent | IRRITATION SCORE | |
|---|---|---|---|
| | | Initial Irritation (1 Hour) | Sustained Irritation (7 Days) |
| E | 6.0 | 3.0 | 0 |
| F | 8.0 | 2.0 | 0 |
| G | 5.0 | 1.3 | 0 |
| H | 4.0 | 6.7 | 0 |
| I | 3.0 | 7.7 | 0.3 |
| Control | 0 | 11.3 | 23.2 |

EXAMPLE 3

Baby bath compositions with and without added bisquaternary ammonium compound and having the formulations indicated below were prepared in a conventional manner by intimately mixing the components.

| | COMPOSITION | | | | | |
|---|---|---|---|---|---|---|
| INGREDIENT | E | F | G | H | I | Control |
| | Percent of Weight | | | | | |
| Tegobetaine J (30%)[1] | 14.84 | 14.84 | 14.84 | 14.84 | 14.84 | 14.84 |
| St. Coco HM Special (24%)[2] | 10.00 | 10.00 | 10.00 | 10.00 | 10.00 | 10.00 |
| DV 674C (32%)[3] | 21.00 | 21.00 | 21.00 | 21.00 | 21.00 | 21.00 |
| Arlacel 20[4] | 0.90 | 0.90 | — | — | — | — |
| Boric Acid (preservative) | 0.50 | 0.50 | 0.50 | 0.50 | 0.50 | 0.50 |
| Benzyl Alcohol (preservative) | 0.10 | 0.10 | 0.10 | 0.10 | 0.10 | 0.10 |
| 15% HCl | pH-7 | pH-7 | pH-7 | pH-7 | pH-7 | pH-7 |
| D&C Yellow #10 (dye) | 0.0017 | 0.0017 | 0.0017 | 0.0017 | 0.0017 | 0.0017 |
| D&C Yellow #6 (dye) | 0.0002 | 0.0002 | 0.0002 | 0.0002 | 0.0002 | 0.0002 |
| Perfume | 0.35 | 0.35 | 0.35 | 0.35 | 0.35 | 0.35 |
| Compound E | 3.0 | 3.0 | — | — | — | — |
| Compound C | 3.0 | 5.0 | 5.0 | 4.0 | 3.0 | — |
| Water | q.s. to 100 | | | | | |

[1]Coconut amidobetaine (Inolex, Philadelphia, Pa.)
[2]2-"Cocoyl"-(sodium carboxymethyl)-1-(2-hydroxyethyl)-2-imidazolium hydroxide (Miranol Chemical Co.).
[3]Tridecyl alcohol ether (4.2) sulfate (Alcolac, Inc., Baltimore, Md.)
[4]Sorbitan monolaurate (ICI America, Atlas Chem. Div., Wilmington, Del.)

The compositions were employed in studies carried out as previously described for the determination of their effect on eye irritation. The results showing extent of initial irritation (1 hour reading) and sustained irritation (7 day reading) are seen in Table II.

| | COMPOSITION | | | |
|---|---|---|---|---|
| INGREDIENT | J | K | L | Control |
| | Percent By Weight | | | |
| Purified Water | 70.175 | 70.175 | 70.175 | 70.175 |
| Versene 100 (39%)[1] | 0.05 | 0.05 | 0.05 | 0.05 |
| DV-674-C (32%) | 12.80 | 12.80 | 12.80 | 12.80 |
| Lonzaine JJ (44%)[2] | 11.00 | 11.00 | 11.00 | 11.00 |
| Polyethyleneglycol-6000 (thickener) | 1.50 | 1.50 | 1.50 | 1.50 |
| Arlamol E (wetting agent)[3] | 0.50 | 0.50 | 0.50 | 0.50 |
| Dowicil 200 (preservative)[4] | 0.10 | 0.10 | 0.10 | 0.10 |
| Benzyl alcohol | 0.30 | 0.30 | 0.30 | 0.30 |
| Fragrance | 0.075 | 0.075 | 0.075 | 0.075 |
| Phosphoric acid (10%) | 0.50 | 0.50 | 0.50 | 0.50 |
| Phosphate buffer | 2.00 | 2.00 | 2.00 | 2.00 |
| Compound E | 1.00 | — | — | — |
| Compound C | — | 1.00 | — | — |
| Compound D | — | — | 1.00 | — |

[1]Na$_4$ EDTA chelating agent (Dow Chemical Co., Midland, Mich.)
[2]Cocoamido sulfobetaine (Lonza, Inc., Fairlawn, N.J.)
[3]Propoxylated stearyl alcohol (ICI America)
[4]Cis isomer of 1-(3-chloroallyl)-3,5,7-triaza-1-azoniaadamantane chloride (Dow Chemical Co.)

The effect of the compositions on eye irritation were determined employing the method previously described. The results show the compositions decreased initial (1 hour) irritation.

TABLE III

| COMPOSITION | QUATERNARY COMPOUND Percent | IRRITATION (1 Hour) |
|---|---|---|
| J | 1.0 | 5.3 |
| K | 1.0 | 5.8 |
| L | 1.0 | 5.5 |
| Control | 0 | 9.8 |

EXAMPLE 4

An experimental aqueous shampoo composition containing 6 percent aqueous cocoamido sulfobetaine, 6 percent tridecyl ether (4) sulfate, 0.5 percent boric acid and 0.1 percent benzyl alcohol was modified in separate operations with ethyleneoxyethylene-bis(dimethyldodecyl ammonium bromide), hepta(ethyleneoxy)ethylene-bis(dimethyl-octadecylammonium bromide), hepta(ethyleneoxy)ethylene-bis(methyl-dioctadecylammonium bromide) and ethyleneoxyethylene-bis(dimethyldocosylammonium gluconate) to produce modified compositions M, N, O and P, respectively. The compositions were tested for ocular irritancy as previously described and compared with control composition containing no bisquaternary ammonium compound. The overall ratings based on consideration of all the individual readings were as follows:

TABLE IV

| COMPOSITION | IRRITATION EVALUATION |
|---|---|
| M | Slight |
| N | Slight |
| O | Slight - moderate |
| P | Slight |
| Control | Severe |

EXAMPLE 5

An experimental aqueous shampoo composition containing 6 percent aqueous cocoamidosulfobetaine solution, 0.5 percent boric acid, and 0.1 percent benzyl alcohol was modified in separate operations with 1.0 percent of ethyleneoxyethylene-bis(dimethyloctadecylammonium bromide) (Compound A) and with ethyleneoxyethylene-bis(dimethyldocosylammonium bromide) (Compound H). The modified compositions thus prepared as well as control compositions containing no bisquaternary ammonium compound were tested for ocular irritancy as previously described. The overall ratings based on consideration of all individual readings were as follows:

TABLE V

| COMPOSITION | IRRITATION EVALUATION |
|---|---|
| Compound A | Moderate |
| Control | Severe |
| Compound H | Slight |
| Control | Severe |

The following examples illustrate compositions suitable for use as cosmetic cleansing compositions of little or no ocular irritancy.

EXAMPLE 6

| INGREDIENT | PERCENT BY WEIGHT |
|---|---|
| N-(3-coconut acylaminopropyl)-N,N-dimethyl-2-aminoacetate | 15.0 |
| Tridecyl alcohol ether (3) sodium sulfate | 15.0 |
| Compound C | 0.50 |
| Preservative | 0.60 |
| Water q.s. to | 100 |
| pH adjusted to 7.0 with dilute (10%) HCl | |

EXAMPLE 7

| INGREDIENT | PERCENT BY WEIGHT |
|---|---|
| 3-(N,N-dimethyl-N-laurylamino)-2-hydroxy-propane-sulfonate | 5.0 |
| Compound A | 0.60 |
| Preservative | 0.60 |
| Water q.s. to | 100 |
| pH adjusted to 7.0 with dilute $H_2SO_4$ | |

EXAMPLE 8

| INGREDIENT | PERCENT BY WEIGHT |
|---|---|
| Tridecyl alcohol ether (3) sodium sulfate | 20.0 |
| Compound C | 4.0 |
| PEG 6000* distearate (Thickner) | 1.0 |
| Preservative | .6 |
| Water q.s. to | 100 |
| pH adjusted to 7.0 with dilute HCl | |

*polyethyleneglycol, av. m.w. 6000

EXAMPLE 9

| INGREDIENT | PERCENT BY WEIGHT |
|---|---|
| N-dodecyl dimethyl glycine | 7.0 |
| Sodium lauryl sulfate | 3.0 |
| Compound E | 2.0 |
| PEG 6000 distearate | 2.0 |
| Preservative | 0.6 |
| Water q.s. to | 100 |
| pH adjusted to 7.0 with dilute HCl | |

EXAMPLE 10

| INGREDIENT | PERCENT BY WEIGHT |
|---|---|
| N-cocoyl(dimethylamino)propane sulfonate | 4.0 |
| Compound A | 0.5 |
| Water q.s. to | 100 |
| pH adjusted to 7.0 with citric acid | |

EXAMPLE 11

| INGREDIENT | PERCENT BY WEIGHT |
|---|---|
| Sodium N-coco-$\beta$-aminopropionate | 5.0 |

| INGREDIENT | PERCENT BY WEIGHT |
|---|---|
| Tridecyl alcohol ether (3) sodium sulfate | 5.0 |
| Compound H | 0.5 |
| Compound C | 1.0 |
| Preservative | 0.6 |
| Water q.s. to | 100 |
| pH adjusted to 6.5 with HCl | |

EXAMPLE 12

| INGREDIENT | PERCENT BY WEIGHT |
|---|---|
| Lexaine J (30%)* | 15.0 |
| Sodium N-cocoyl-N-methyltaurate | 5.0 |
| Compound D | 2.0 |
| Preservative | 0.60 |
| Water q.s. to | 100 |
| pH adjusted to 4.0 with HCl | |

*N-(3-coconut acylamino-N,N-dimethyl aminoacetate (Inolex)

EXAMPLE 13

| INGREDIENT | PERCENT BY WEIGHT |
|---|---|
| Lonzaine C S (40%)* | 15.0 |
| 2 cocoyl-1-(sodium carboxymethyl)-1-(2hydroxyethyl)-2-imidazolium hydroxide | 2.0 |
| Tridecyl alcohol ether (3) sodium sulfate | 5.0 |
| Eisoca(ethyleneoxy)ethylene-bis (dodosyl-dimethylammonium bromide) | 3.0 |
| Preservative | 0.60 |
| Water q.s. to | 100 |
| pH adjusted to 7.2 with dilute $H_2SO_4$ | |

*3-(N,N-dimethyl-N-laurylamino)-2-hydroxypropane-sulfonate (Lonza)

EXAMPLE 14

| INGREDIENT | PERCENT BY WEIGHT |
|---|---|
| Miranol HM (24%) | 20.0 |
| Cocoyl ester of sodium isethionate | 2.0 |
| Triconta(ethyleneoxy)ethylene bis(dimethyl-octadecylammonium bromide) | 2.0 |
| Compound H | 0.20 |
| Preservative | 0.60 |
| Dye | 0.001 |
| Perfume | 0.01 |
| Water q.s. to | 100 |

*Coco-imadazoline (Miranol Chemical Co.)

EXAMPLE 15

The following is an example of a composition for a lotion shampoo.

| INGREDIENT | PERCENT BY WEIGHT |
|---|---|
| Igepon TM-43 (24%)* | 40.0 |
| Coco-amido-betaine | 5.0 |
| Triconta(ethyleneoxy)ethylene-bis(docosyl-dimethylammonium bromide) | 2.0 |
| Preservative | 0.60 |
| Dye | 0.001 |
| Perfume | 0.01 |
| Water q.s. to | 100 |
| pH adjusted to 7.5 with citric acid | |

*Sodium N-myristoyl N-methyltaurate (GAF Corp., N.Y.)

EXAMPLE 16

The following is an example of a composition suitable as a cream shampoo.

| INGREDIENT | PERCENT BY WEIGHT |
|---|---|
| Igepon TM-43 (24%) | 30.0 |
| Igepon AM-78 (80%)* | 10.0 |
| Dodecyl benzene sulfate, Na salt | 1.0 |
| Compound C | 4.0 |
| Preservative | 0.60 |
| Dye | 0.001 |
| Perfume | 0.01 |
| Water q.s. to | 100 |
| pH adjusted to 7.0 with citric acid | |

*Myristic acid ester of sodium isethionate (GAF)

EXAMPLE 17

The following is an example of a gel cleanser composition.

| INGREDIENT | PERCENT BY WEIGHT |
|---|---|
| N-(3-coconut acylaminopropyl)-N,N-dimethyl-2-aminoacetate | 20.0 |
| Sodium lauryl ether sulfate | 20.0 |
| Pentadeca(polyethyleneoxy)ethylene bis(dimethyl-tetradecylammonium bromide) | 4.0 |
| Preservative | 0.60 |
| Dye | 0.001 |
| Perfume | 0.01 |
| Water q.s. to | 100 |
| pH adjusted to 7.0 with dilute HCl | |

EXAMPLE 18

| INGREDIENT | PERCENT BY WEIGHT |
|---|---|
| N-cocoyl(dimethylamino)-propane sulfonate | 5.0 |
| Sodium lauryl ether sulfate | 2.0 |
| Protein hydrolysate (Maypon, 30%)[1] | 3.0 |
| Compound H | .80 |
| Preservative | .60 |
| Dye | .001 |
| Perfume | .01 |
| Water q.s. to | 100 |
| pH adjusted to 6.0 with citric acid. | |

[1]product of Stephan Chemical Co., Northfield, Ill.

EXAMPLE 19

| INGREDIENT | PERCENT BY WEIGHT |
|---|---|
| Nonyl phenol polyoxyethylene (3) sodium sulfate | 3.0 |
| Cocoyl sarcosine | 2.0 |
| N-dodecyl dimethyl glycine | 2.0 |
| Tri(ethyleneoxy)ethylene bis(docosyl-dimethylammonium bromide) | 2.50 |

| INGREDIENT | PERCENT BY WEIGHT |
|---|---|
| PEG 6000 distearate | 0.50 |
| Preservative | 0.60 |
| Dye | 0.001 |
| Perfume | 0.01 |
| Water q.s. to | 100 |
| pH adjusted to 7.5 with dilute HCl | |

EXAMPLE 20

| INGREDIENT | PERCENT BY WEIGHT |
|---|---|
| Miranol C2M (34%)* | 30.0 |
| Octyl phenol polyoxyethylene sulfonate, Na salt | 5.0 |
| Tri(ethyleneoxy)ethylene-bis(dimethyl-octadecyl ammonium bromide) | 2.0 |
| PEG 6000 distearate | 2.0 |
| Preservative | 0.60 |
| Dye | 0.001 |
| Perfume | 0.01 |
| Water q.s. to | 100 |
| pH adjusted to 7.0 with dilute HCl | |

*Coco-imidazolium chloride (Miranol Chemical Co.)

EXAMPLE 21

| INGREDIENT | PERCENT BY WEIGHT |
|---|---|
| Disodium lauryl sulfosuccinate | 5.0 |
| $C_{11}$ alpha olefin sulfonate | 2.0 |
| Disodium monoleamido sulfosuccinate | 2.0 |
| Compound C | 2.0 |
| PEG 6000 distearate | 1.50 |
| Preservative | 0.60 |
| Dye | 0.001 |
| Perfume | 0.01 |
| Water q.s. to | 100 |
| pH adjusted to 7.5 with dilute HCl | |

EXAMPLE 22

| INGREDIENT | PERCENT BY WEIGHT |
|---|---|
| Tridecyl alcohol ether (3) sodium sulfate | 20.0 |
| Hepta(ethyleneoxy)ethyl-bis-(diethyl-octadecyl ammonium bromide) | 4.0 |
| PEG 6000 distearate | 1.0 |
| Preservative | 0.60 |
| Water q.s. to | 100 |
| pH adjusted to 7.0 with dilute HCl | |

EXAMPLE 23

| INGREDIENT | PERCENT BY WEIGHT |
|---|---|
| Tridecyl alcohol ether (3) sodium sulfate | 20.0 |
| Hepta(ethyleneoxy)ethyl-bis-(dipropyl-octadecyl ammonium bromide) | 4.0 |
| PEG 6000 distearate | 1.0 |
| Preservatives | 0.60 |
| Water q.s. to | 100 |
| pH adjusted to 7.0 with dilute HCl | |

EXAMPLE 24

| INGREDIENT | PERCENT BY WEIGHT |
|---|---|
| Tridecyl alcohol ether (3) sodium sulfate | 20.0 |
| Hepta(ethyleneoxy)ethyl-bis (dimethyl-hexacosyl ammonium bromide) | 4.0 |
| PEG 6000 distearate | 1.0 |
| Preservative | 0.60 |
| Water q.s. to | 100 |
| pH adjusted to 7.0 with dilute HCl | |

EXAMPLE 25

| INGREDIENT | PERCENT BY WEIGHT |
|---|---|
| Tridecyl alcohol ether (3) sodium sulfate | 20.0 |
| Penta(propyleneoxy)propylene-bis (dimethyl-octadecyl ammonium bromide | 4.0 |
| PEG 6000 distearate | 1.0 |
| Preservatives | 0.60 |
| Water q.s. to | 100 |
| pH adjusted to 7.0 with dilute HCl | |

EXAMPLE 26

Cleansing compositions with and without alkylene oxylated bisquaternary ammonium compounds having the components indicated below were prepared.

| | COMPOSITION | | |
|---|---|---|---|
| | A | B | C |
| INGREDIENT | PERCENT BY WEIGHT | | |
| Compound AA | 6.0 | 6.0 | 6.0 |
| Compound C | — | 2.0 | — |
| Compound E | — | — | 2.0 |
| Deionized Water | 94 | 92 | 92 |

The compositions were employed to determine eye irritation by a modified Draize method and scored as previously described. The results were as follows:

TABLE VI

| | IRRITATION SCORE | | | | | |
|---|---|---|---|---|---|---|
| Composition | 1 Hr. | 24 Hrs. | 48 Hrs. | 72 Hrs. | 96 Hrs. | Day 7 |
| A (Control) | 13.7 | 30.8 | 32.2 | 56.8 | 51.2 | 39.2 |
| B | 14.7 | 17.8 | 18.8 | 28.0 | 30.5 | 13.7 |
| C | 13.5 | 12.7 | 15.2 | 30.0 | 15.7 | 12.5 |

As noted from TABLE VI above, the compositions containing the alkylene oxylated bisquaternary ammonium compounds exhibit significantly reduced eye irritation when compared to the control not containing said compounds.

The following examples illustrate compositions suitable for use as cosmetic cleansing compositions exhibiting low ocular irritancy.

EXAMPLE 27

| INGREDIENT | PERCENT BY WEIGHT |
|---|---|
| Compound AA | 15.0 |
| Tridecyl alcohol (3) ether sodium sulfate | 15.0 |
| Compound C | 0.5 |
| Preservatives | 0.6 |
| Water q.s. to | 100 |
| pH adjusted to 7.0 with dilute (10%) HCL | |

EXAMPLE 28

| INGREDIENT | PERCENT BY WEIGHT |
|---|---|
| Compound CC | 5.0 |
| Compound A | 1.0 |
| Preservatives | 0.6 |
| Water q.s. to | 100 |
| pH adjusted tp 7.0 with dilute (10%) HCL | |

EXAMPLE 29

| INGREDIENT | PERCENT BY WEIGHT |
|---|---|
| Compound DD | 6.0 |
| Sodium lauryl sulfate | 4.0 |
| Compound E | 2.0 |
| PEG 6000 distearate | 2.0 |
| Preservatives | 0.6 |
| Water q.s. to | 100 |
| pH adjusted to 6.5 with dilute $H_2SO_4$ | |

EXAMPLE 30

| INGREDIENT | PERCENT BY WEIGHT |
|---|---|
| Compound BB | 6.0 |
| Compound H | 1.0 |
| Compound C | 1.0 |
| Water q.s. to | 100 |
| pH adjusted to 6.5 with dilute (10%) HCL | |

EXAMPLE 31

| INGREDIENT | PERCENT BY WEIGHT |
|---|---|
| Sodium N-coco beta-amino proprionate | 5.0 |
| Compound AA | 5.0 |
| Compound C | 2.0 |
| Preservatives | 0.6 |
| Water q.s. to | 100 |
| pH adjusted to 6.5 with dilute (10%) HCL | |

EXAMPLE 32

| INGREDIENT | PERCENT BY WEIGHT |
|---|---|
| Compound EE | 5.0 |
| Sodium N-acyl N-methyl taurine | 5.0 |
| Compound D | 2.0 |
| Preservative | 0.6 |
| Water q.s. to | 100 |
| pH adjusted to 4.0 with dilute (10%) HCL | |

EXAMPLE 33

| INGREDIENT | PERCENT BY WEIGHT |
|---|---|
| Compound FF | 7.5 |
| Amido sultaine | 7.5 |
| Tridecyl alcohol (3) ether sodium sulfate | 3.0 |
| Compound H | 2.0 |
| Preservatives | 0.6 |
| Water q.s. to | 100 |
| pH adjusted to 7.0 with dilute (10%) HCL | |

EXAMPLE 34

| INGREDIENT | PERCENT BY WEIGHT |
|---|---|
| Compound GG | 10.0 |
| Acyl ester of sodium isethionate | 5.0 |
| Compound H | 2.5 |
| Preservatives | 0.6 |
| Water q.s. to | 100 |
| pH adjusted to 7.0 with dilute (10%) HCL | |

EXAMPLE 35

| INGREDIENT | PERCENT BY WEIGHT |
|---|---|
| Igepon TM-43 | 40.000 |
| Compound HH | 5.000 |
| Compound C | .1.000 |
| Preservatives | 0.600 |
| Dyes | 0.001 |
| Fragrance | 0.200 |
| Water q.s. to | 100 |
| pH adjusted to 7.5 with citric acid | |

EXAMPLE 36

| INGREDIENT | PERCENT BY WEIGHT |
|---|---|
| Compound AA | 6.000 |
| Lauric myristic imidazoline | 6.000 |
| Sodium lauryl (3) ether sulfate | 2.000 |
| Sodium lauric/myristic ether carboxylate | 12.000 |
| Compound D | 1.000 |
| Thickner | 0.500 |
| Propylene glycol | 2.000 |
| Preservatives | 0.600 |
| Dyes | 0.001 |
| Fragrance | 0.200 |
| Water q.s to | 100 |
| pH adjusted to 7 with dilute (10%) HCL | |

EXAMPLE 37

| INGREDIENT | PERCENT BY WEIGHT |
|---|---|
| Compound JJ | 10.00 |
| Sodium lauryl (3) ether sulfate | 4.00 |
| Compound H | 1.00 |
| Preservatives | 0.60 |
| Water q.s. to | 100 |
| pH adjusted to 7.0 with dilute H₂SO₄ | |

In addition to the preferred embodiments described herein, other arrangements and variations within the spirit of the invention and the scope of the appended claims will occur to those skilled in the art.

EXAMPLE 38

| INGREDIENT | PERCENT BY WEIGHT |
|---|---|
| Compound KK | 5.00 |
| Lauric/myristic imidazoline | 5.00 |
| Sodium lauryl (3) ether sulfate | 4.00 |
| Compound D | 4.00 |
| Preservatives | 0.60 |
| Water q.s. to | 100 |
| pH adjusted to 7.0 with dilute (10%) HCL | |

EXAMPLE 39

| INGREDIENT | PERCENT BY WEIGHT |
|---|---|
| Igepon TM-43 | 40.00 |
| Compound BB | 5.00 |
| Compound C | 1.50 |
| Preservatives | 0.60 |
| Water q.s. to | 100 |
| pH adjusted to 7.0 with dilute (10%) HCL | |

The foregoing examples are merely illustrative of the more preferred of the modified cleansing compositions of the present invention which are extremely low in irritancy to the eyes and skin and which further have good foaming and cleansing properties. By modifying anionic and/or amphoteric detergent compositions with the alkylenoxylated bisquaternary ammonium compounds as illustrated, cleansing compositions of very low irritancy may be achieved without sacrificing cleansing efficiency.

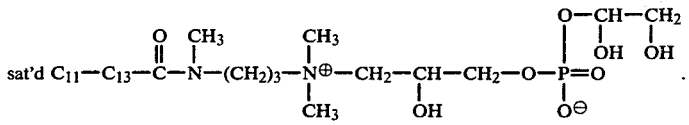

What is claimed is:

1. A cosmetic cleansing composition comprising a detergent component in admixture with an alkyleneoxylated bisquaternary ammonium compound component wherein said detergent component comprises at least one amphoteric detergent selected from the group consisting of

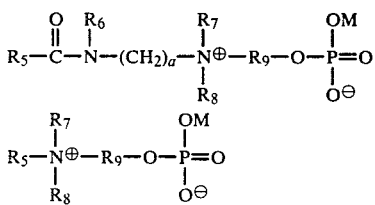

(a)

(b)

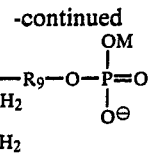

(c)

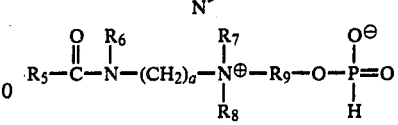

(d)

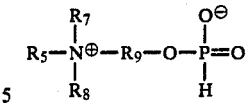

(e)

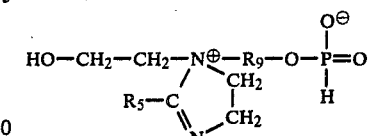

(f)

wherein $R_5$ is straight or branched chain alkyl, alkenyl, arylalkyl or cycloalkyl containing from 6 to 26 carbon atoms; $R_6$ is hydrogen, straight or branched chain alkyl, alkenyl, cycloalkyl or hydroxyalkyl containing from 1 to 6 carbon atoms; $R_7$ and $R_8$ may be the same or different and are straight or branched chain alkyl or hydroxyalkyl containing from 1 to 6 carbon atoms or a polyoxyalkylene ether radical of the formula

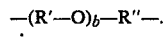

wherein
$R'$ and $R''$ are alkylene and alkyl, respectively, containing from 1 to 4 carbon atoms and b is an integer from 2 to 10;

$R_9$ is straight or branched chain alkylene or hydroxyalkylene containing from 1 to 6 carbon atoms; M is straight or branched chain alkyl or hydroxyalkyl containing from 1 to 6 carbon atoms, polyhydroxyalkyl containing from 1 to 6 carbon atoms, alkali metal, alkaline earth metal or a substituted ammonium compound selected from mono-, or di- or triethanolamine; and a is an integer from 1 to 5; said alkyleneoxylated bisquaternary ammonium compound component contains one or more compounds represented by the formula

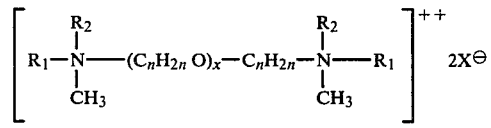

wherein $R_1$ is an aliphatic radical of from about 10 to about 26 carbon atoms, $R_2$ is methyl, ethyl, propyl or $R_1$, X is an anion, n is 2 or 3, and x is an integer of from 1 to about 30; and said detergent component is present in an amount of from about 4 percent to 40 percent by weight of the composition and the weight ratio of said bisquaternary ammonium compound to detergent is from about 0.01:1 to about 0.3:1.

2. The composition of claim 1 containing in addition at least one anionic detergent.

3. A composition according to claim 1 wherein said alkyleneoxy bisquaternary ammonium compound component is represented by the formula

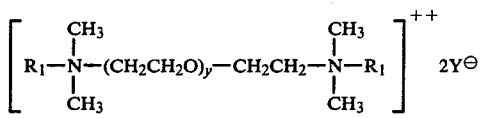

wherein $R_1$ is an aliphatic radical of from about 10 to about 26 carbon atoms, Y is halide, and y is an integer of from 7 to about 14.

4. A composition according to claim 3 wherein the bisquaternary compound is hepta(ethyleneoxy)ethylene-bis-(docosyl-dimethylammonium bromide).

5. A composition according to claim 3 wherein the bisquaternary compound is dodeca(ethyleneoxy)ethylene-bis-(docosyl-dimethylammonium bromide).

6. A composition according to claim 1 wherein the detergent component is a shampoo composition.

7. A composition according to claim 1 wherein the detergent component is a baby bath composition.

8. A composition according to claim 1 wherein said amphoteric detergent is represented by formula (a) therein.

9. A composition according to claim 8 wherein said detergent is of the formula

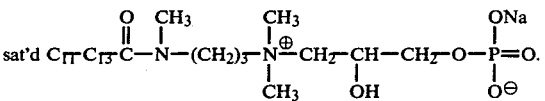

10. A composition according to claim 8 wherein said detergent is of the formula